United States Patent [19]
Jacobs et al.

[11] Patent Number: 6,049,794
[45] Date of Patent: Apr. 11, 2000

[54] SYSTEM FOR SCREENING OF MEDICAL DECISION MAKING INCORPORATING A KNOWLEDGE BASE

[76] Inventors: Charles M. Jacobs, 255 West St., Northborough, Mass. 01532; Josephine A Lamprey, 15 Pine Rd., North Hampton, N.H. 03862; A. Jacqueline Mitus, 24 Pelton St., West Roxbury, Mass. 02132; Alec P Karys, 81 Shadow Oak Dr., Sudbury, Mass. 01776; David W Baird, 590 Linden St., Boylston, Mass. 01505; Thomas W. Upton, 1104 Elm St. Unit 4, Marlborough, Mass. 01752

[21] Appl. No.: 08/988,368
[22] Filed: Dec. 9, 1997
[51] Int. Cl.$^7$ ................................................... G06F 17/00
[52] U.S. Cl. .............................. 706/45; 706/46; 706/47
[58] Field of Search ................................. 706/45, 46, 47; 705/2, 3

[56] References Cited

U.S. PATENT DOCUMENTS

| | | | |
|---|---|---|---|
| 4,170,987 | 10/1979 | Anselmo et al. | 600/475 |
| 4,731,725 | 3/1988 | Suto et al. | 706/46 |
| 5,007,429 | 4/1991 | Treatch et al. | 600/700 |
| 5,357,427 | 10/1994 | Langen et al. | 600/300 |
| 5,583,758 | 12/1996 | McIlroy et al. | 705/2 |
| 5,594,638 | 1/1997 | Edwin | 705/3 |
| 5,615,112 | 3/1997 | Sheng et al. | 707/104 |
| 5,878,746 | 3/1999 | Lemelson et al. | 128/653.1 |
| 5,906,578 | 5/1999 | Rajan et al. | 600/424 |
| 5,911,132 | 6/1999 | Sloane | 705/3 |

OTHER PUBLICATIONS

Anderson, "Clearing the way fro physicians use of clinical information systems", Comm. of the ACM vo. 40, No. 8, pp. 83–90, Aug. 1997.

Fink et al, "The disease progression explorer: risk assessment support in chronic, multifactorial disease", SAC ACM pp. 46–51, Apr. 1999.

Gobbetti et al, "interactive virtual angioscopy", IEEE, pp. 435–461, 1998.

Heinlein et al, "Representation of medical guidelines using a classification based system", CIKM ACM pp. 415–422, Mar. 1994.

Fala et al, "Applying expert system to health care management", ACM pp. 237–241, 1995.

Lusted, "Some roots of clinical decision making", ACM pp. 165–193, Sep. 1987.

Heinlien et al., "Representation of medical guidlines using a classification based system", CIKM ACM, pp. 415–422, Nov. 1994.

Carenini et al., Generating explations in contex, Intelligent user interface, ACM, pp. 175–183, 1993.

*Primary Examiner*—Paul R. Lintz
*Assistant Examiner*—Anil Khatri
*Attorney, Agent, or Firm*—Mark P. White

[57] ABSTRACT

A System for screening of medical decision making is described. The system runs on a personal computer, and incorporates a knowledge base containing the data required to perform the screening, as well as the rules to be incorporated. The knowledge base is organized into criteria sets subdivided into categories, which include clinical specialties, such as surgery, and imaging, or a level of care, or a body system. The criteria sets are further subdivided into interventions, review types, and levels of care. Finally, within each subdivision, the user selects criteria points which are representations of the patient's clinical condition. Upon selection of the criteria points, the system will indicate whether or not a selected method of treatment is medically appropriate or not. The review process is recorded for subsequent examination.

16 Claims, 22 Drawing Sheets

FIG. 5

InterQual --- AutoBook 2 for Windows

File  Help

InterQual®  Gen Note | Cancel Review | Report | Review Complete | New Review Patient Information | Category--ISP | Criteria Subset | Case Notes | Med.Review Notes Info Note | Man. Note

Criteria NOT Met

Coronary Angiogram

☆ ◁ 100  Severe cardiac ischemia by stress test
          ONE
☆ ▷ 110  Exercise treadmill test
☆ ▷ 120  Nuclear stress test
☆ ▷ 130  Stress echo
☆ ▷ 140  Persantine nuclear stress test
☆ ▷ 150  Dobutamine echo
☆ ▷ 160  Dobutamine nuclear stress test ☆ ▷ 200  Unstable angina
☆ ▷ 300  Post MI angina/ischemia
☆ ▷ 400  Post PTCA
☆ ▷ 500  CAD evaluation prior to major surgery
☆ ▷ 600  Arrhythmia
[ ] 700  New onset acute CHF by chest x-ray & Hx & PE
☆ ▷ 800  Acute MI
☆ ▷ 900  Newly discovered LV systolic dysfunction

FIG. 9

ISP - Review Session

| | | | |
|---|---|---|---|
| Review ID | 12d | Patient ID | 210d |
| Patient Name | Doe, John | Patient Gender | M | Patient Age 62 |
| Provider ID | 544 | Main ICD-9 | OS | Ref: LOS  QHS |
| Provider Name | Paradym Med Srv | Search ICD-9 | | |
| Facility Code | 0S | CPT Code | | |
| Overview Date | 12/0/1997 | | | |
| Review Date | 12/0/1997 | Target Review Date | | |
| Review Time | 10:20:51 PM | | | |
| Reviewer ID | 0S | | | |
| Procedure | Coronary Angiogram | | | |
| Clinical Guides | Met | | | |

Selected  Criteria  Points

△ ✓ 100 Severe cardiac ischemia by stress test
       ONE
△ ✓ 110 Exercise treadmill test
       ONE
 [✓]  111 Horizontal ST depressions >= 2mm in 2 continuous leads
 [ ]  112 Chest pain within first 10 minutes —110
 [ ]  113 Systolic BP drop >= 10mm Hg within first 10 minutes —112
▽      114 VT —114
▽      120 Nuclear stress test
       130 Stress echo 2 of 2    Cancel   Close    16 of 16   Total: 16   100%

FIG. 11

ISP - Review Session

| | | | | |
|---|---|---|---|---|
| Review ID | 12d | Patient ID | 210d | |
| Patient Name | Doe, John | Patient Gender | M | Patient Age 62 |
| Provider ID | 544 | Main ICD-9 | OS | |
| Provider Name | Paradym Med Srv | Search ICD-9 | | Ref: LOS QHS |
| Facility Code | OS | CPT Code | | |
| Overview Date | 12/0/1997 | | | |
| Review Date | 12/0/1997 | Target Review Date | | |
| Review Time | 10:20:51 PM | | | |
| Reviewer ID | OS | | | |
| Procedure | Coronary Angiogram | | | |
| Clinical Guides | Met | | | |

Review Outcome:
[ ] Approved      [ ] Request withdrawn
[ ] Referred for medical review      [ ] Review interrupt
[ ] Awaiting more information      [ ] Alternate Prac/Ref/LOC selected Reviewer Referral Codes:
[ ] Imaging NOT met
[ ] Symptoms NOT met
[ ] Findings NOT met
[ ] Clinical management NOT met
[ ] Indications not included in criteria
[ ] Procedure/diagnosis not included in criteria
[ ] Medical review mandated for this procedure

InterQual --- AutoBook 2 for Windows

File  Help

InterQual®  | ISDa Help | Cancel Review | Report | Review Complete | Edit Review |

Patient Information | Category--ISDa | Pre-Admit Review | Case Notes — 184 | Med.Review Notes |

Referral Codes
- ☐ Surgical service delay
- ☒ Diagnostic service delay — 190
- ☐ Treatment service delay
- ☐ Physician service delay
- ☐ CM/DP/SS service delay
- ☐ Discharge delay, Attending agrees with ALOC
- ☐ ALOC bed not available
- ☐ ALOC not available
- ☐ Service not available
- ☐ Patient/SO refuses transfer/discharge
- ☐ Home/homecare not organized
- ☐ Discharge delay, social factors
- ☐ Patient refuses treatment
- ☐ Preoperative day(s)
- ☐ Other Review Outcome: Referred for Medical review — 188

- Approved
- Referred for Medical review — 192
- Awaiting more information
- Request withdrawn
- Review Interrupt
- Alternate procedure/referral/LOC selected Target Review Date Alt. Level of Care Variance Days Case Note InterQual --- AutoBook 2 for Windows File  Help InterQual®  Gen. Note  Cancel Review  Report  Review Complete  New Review Patient Information  Category--IWC-IRM  Criteria Subset  Case Notes  Med.Review Notes

Criteria Met  Info Note  Man. Note

Cauda Equina Syndrome

✓ 100 Suspended cauda equina syndrome
  ALL
✓ 110 Sx/findings
     ONE
☆ [✓] 111 Neurogenic claudication by Hx
☆ [✓] 112 Loss of bowel/bladder control by Hx [U]
☆ [✓] 113 Diffuse weakness in lower extremities by PE
☆ [✓] 114 Diffuse sensory deficit in lower extremities
           by PE
☆ [✓] 115 Diffuse pain in lower extremities by Hx
☆ [✓] 120 Urgent surgical consultation ordered
☆ [✓] 130 Individualized CM recommended 200 Cauda equina compression

InterQual --- AutoBook 2 for Windows

File  Help

InterQual® | ISDa Help | Cancel Review | Report | Review Complete | Edit Review Patient Information | Category--ISP | Criteria Subset | Case Notes | Med.Review Notes

— 184
— 188

Referral Codes
- ☐ Imaging NOT met
- ☐ Symptoms NOT met
- ☐ Findings NOT met
- ☐ Clinical management NOT met
- ☐ Indication not included in criteria
- ☐ Procedure/diagnosis not included in criteria
- ☐ Medical review mandated for this procedure
- ☐ Medical Review Criteria Note met
- ☐ Recommended treatment not available
- ☐ Patient refuses clinical management
- ☐ Condition precludes rec. clin. Management
- ☐ Setting inappropriate for procedure
- ☐ Reviewer discretion
- ☐ Other Review Outcome: Approved Target Review Date:

Ref LOS:

Case Note:

SYSTEM FOR SCREENING OF MEDICAL DECISION MAKING INCORPORATING A KNOWLEDGE BASE

BACKGROUND OF THE INVENTION

1. Field of the Invention

The present invention relates to the use of knowledge base systems for the purpose of screening and verifying the results of decision making processes, and more particularly to such systems for decision-making processes in the context of health care.

2. Description Relative to the Prior Art

In the field of health care, as in many other fields involving the accumulation and application of masses of information, the use of artificial intelligence has been looked to as a means of automatic decision making. Artificial intelligence has not yet fulfilled its promise in this regard, however. No such systems provide the reliability required to circumvent the human decision-making process.

However, not withstanding the failures of these systems, artificial intelligence has been used effectively to augment the human decision-making process, rather than replace it. The key to effective use of these systems is constant checking and verification of the computer-generated results by human experts.

Common implementations of such automatic systems include the use of Knowledge bases in computer programs known as "Expert Systems." These systems are known in the art to provide an interactive means of problem solving by accessing information in a user-friendly environment.

In expert systems, information is organized in data trees in which then can be entered by the user at any level. The data is generally arranged hierarchically, so that more detail is derived as the user moves farther toward the tips of tree branches, with more generality toward the root of the tree. In addition to the tree-structured data organization, the knowledge base contains rules for dealing with the data, and for proceeding further down the tree based on the history of the user's current activity.

Such expert systems attempt to emulate human intelligence, and the efficacy of the expert system is dependent on the data contained within the knowledge base, as well as the rules for dealing with this data, and these data and rules must be input prior to use of the system.

To use the expert system, the user begins at a low level, at the "root" of the data tree. At each branch the user makes a decision, and, based on the rules of the knowledge base, the system will give the user a number of specific choices as to how to proceed. The information at the root of the tree is quite general, but as the user continues away from the root the information becomes more and more specific.

Many attempts have been made to utilize such expert systems in the health care setting. In particular, U.S. Pat. No. 5,583,758 describes such a system which provides decisions based on patient data, together with a knowledge base. The results provided by the system are then subjected to review by the health care experts.

Diagnosis systems such as the patent described above suffer from several problems, however. The automated system makes a decision, without providing a continuous rationale for how such decision was made. The decision tree may be thought of as a complex road system, with decisions appearing as branches in the road. Once a wrong branch is taken, for any reason, the decision will probably be wrong.

Furthermore, such systems require frequent updating of the knowledge base. Such updating requires highly-trained medical personnel and computer programmers, and is both time consuming and expensive.

Other approaches to automated assistance in health care decision-making use a statistical data approach. Such systems use statistical calculations to assess the probability that a particular decision will be correct. Examples of statistical systems include Brown et al., MEDICAL STATISTICAL ANALYZING METHOD; PROCESS OF MONITORING PATIENT VITAL SIGNS, U.S. Pat. No. 5,199,439, Altschuler et al., INTERACTIVE STATISTICAL SYSTEM AND METHOD FOR PREDICTING EXPERT DECISIONS, U.S. Pat. No. 5,005,143, and Saito Katsuyoshi et al., DATA PROCESSING SYSTEM WHICH SUGGESTS A PATTERN OF MEDICAL TESTS TO REDUCE THE NUMBER OF TESTS NECESSARY TO CONFIRM OR DENY A DIAGNOSIS, U.S. Pat. No. 4,731,725. Relying on statistical data is an important diagnostic approach, but it is not effective in dealing with cases which fall at the outer ends of the statistical distribution.

The present invention is significantly different from the previous systems in several ways. First, the current system does not attempt to make any diagnosis, but rather acts as a screen or "gate keeper" to alert the decision makers that a proposed intervention or level of care does not meet the pre-determined criteria.

Secondly, the current system is designed so that the user inputting the data to the system need not be the ultimate decision maker. Typically, the original user is a nurse reviewer. Users may include any of the following, however:

a) nurse reviewer;

b) physician assistant;

c) physician;

d) medical director;

e) chief medical officer; and f) other health care workers who have been trained in the use of the system.

Thirdly, the current system provides constant feedback to show the user how the system makes its decisions, displaying the rules used, and displaying when the criteria are met and when they are not met.

Fourthly, the present system provides additional information in the form of notes and information and appropriate points in the decision process, and further categorizing this information into mandatory notes, which are automatically presented to the user, and informational notes, which may or may not be read at the user's discretion, as well as other categories of notes.

Finally, the present system provides comprehensive user level and management level reports which may be reviewed by the decision maker, typically the doctor in charge of the case, or, alternatively, a group or panel of reviewers or their managers. The reviewer may then re-enact the steps of the decision process, reviewing the exact nature of the decisions made by the system at each point in the decision process.

SUMMARY OF THE INVENTION

A general object of the current invention is to provide a screening system to verify medical decisions. A specific object is to implement this system by means of a knowledge base computer program. A further specific object is to implement this system in such a way as to make the decision-making process transparent to the user.

According to one aspect of the invention, a computer-based medical screening system verifies an intended course of action regarding a patient having a clinical situation. The system includes a knowledge base of medical information organized into criteria sets. Each such criteria set contains data and rules for determining when treatment is medically appropriate. The system includes means for inputting patient information and means for selecting a clinical specialty or body system. It also includes means for selecting a procedure within the selected clinical specialty or body system, means for selecting an indication within the selected procedure, means for selecting criteria points within the selected indication based on the patient's clinical situation and computer processing means for determining whether or not the intended course of action is medically appropriate.

According to another aspect of the invention, the criteria sets further include Intensity of Service, Severity of Illness, and Discharge screens for adults, and Intensity of Service, Severity of Illness, and Discharge screens for pediatric patients. The criteria sets also include indications for imaging studies and X-rays, indications for surgery and procedures, indications for primary and specialty care management, and surgical indications monitoring.

According to still another aspect of the invention, the system further includes means for including mandatory review notes in the criteria sets. It also includes means for associating the mandatory review notes with procedures and indications. And it further includes means for outputting the mandatory review notes upon selection of an associated procedure or indication.

According to still another aspect of the invention, the system further includes means for including discretionary review notes in the criteria sets and means for associating the discretionary review notes with procedures and indications. It also includes means for indicating the presence of said discretionary review notes in association with a selected procedure or indication, and means for requesting the display of the discretionary review notes.

According to yet another aspect of the invention, the system further includes means for displaying the rules for meeting the criteria for an intended course of action in conjunction with the procedures and indications selected.

According to a final aspect of the invention, the system further includes means for recording the steps of the review process, means for playback of the steps of the review process, and means for editing the inputs to the review process.

BRIEF DESCRIPTION OF THE DRAWINGS

These, and further features of the invention, may be better understood with reference to the accompanying specification and drawings depicting the preferred embodiment, in which:

FIG. 5 depicts the Patient Information screen.

FIG. 9 depicts the Procedure/Indication screen for a sample ISP review.

FIG. 11 depicts the first page of the Review Session screen for a sample ISP review.

FIG. 12 depicts the second page of the Review Session screen for a sample ISP review.

FIG. 19 depicts a sample Case Note screen.

FIG. 21 depicts the indications screen for an Indications for Worker's Compensation criteria set.

FIG. 22 depicts a Case Notes screen, with an Approved Review Outcome selected.

DETAILED DESCRIPTION OF THE PREFERRED EMBODIMENTS

Definitions

In the following description, certain terms of art will be used which are described as follows:

I. Categories: Each criteria set is divided into categories. A category may be a clinical specialty, such as surgery, imaging, etc., a level of care, or a body system.

II. Titles: Categories consist of titles, or clinical topics. Titles may be either a test, a procedure, or a clinical problem warranting referral. It may be a clinical activity proposed to a patient, or one already provided to a patient. Titles display when a category is selected in AUTOBOOK 2. General or mandatory notes are available at many titles.

III. Criteria: Criteria are objective, patient-specific clinical information used to conduct reviews. Criteria display on AUTOBOOK 2 screens when a title is selected. Criteria involve four main elements:
1. Indications—reasons for performing a procedure, test, or referral. Indications are numbered on the AUTOBOOK 2 screens.
2. Criteria points—representations of the patient's clinical condition.
3. Rules—the logic decisions which determine what criteria points are needed to meet criteria.
4. Notes—a display of pertinent review instructions and clinical information.

Figure 1:
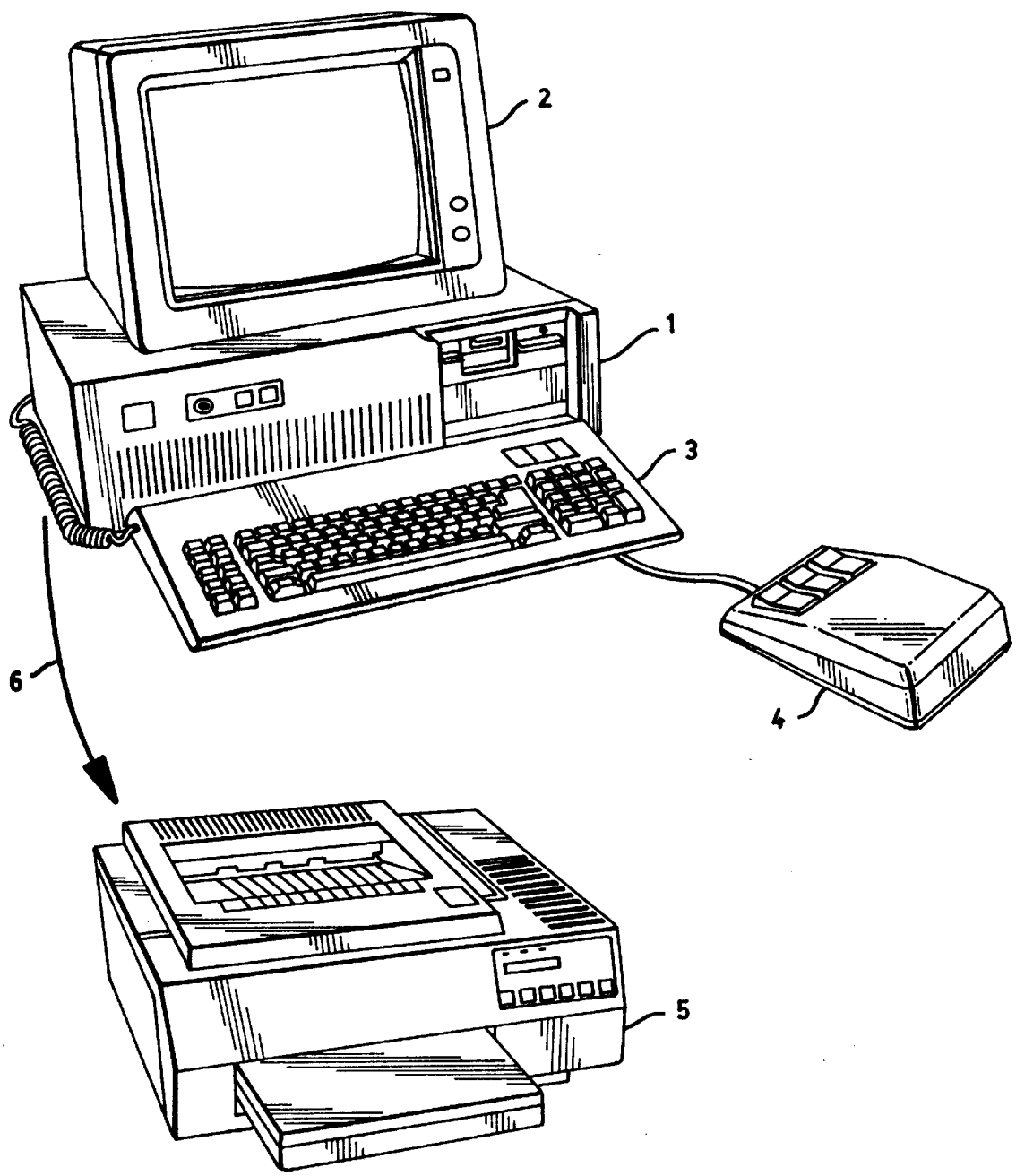
FIG. 1 depicts the hardware required to support the operation of the preferred embodiments.

The current invention operates in its preferred embodiments, by means of a software system that operates on a general purpose computer commonly known as a PC, or IBM clone system, as shown in FIG. 1. The computer system includes a computer cabinet, 1, which contains the central processing unit, RAM memory, graphics adapter, printer controller, hard disk and controller, and mouse controller, none of which are shown. The central processor must be, at a minimum, an Intel® 80486 or equivalent. At least 8 MB of RAM are required for proper operation, while at least 16 MB are recommended.

Also included in the computer hardware are the monitor 2, keyboard 3, mouse 4, and printer 5.

The software of the preferred embodiments requires either a WINDOWS 3.1® or higher operating system, WINDOWS95® or higher, or WINDOWS NT® operating systems.

The preferred embodiments require a minimum of 12 MB space on the hard disk to operated properly.

Figure 2:
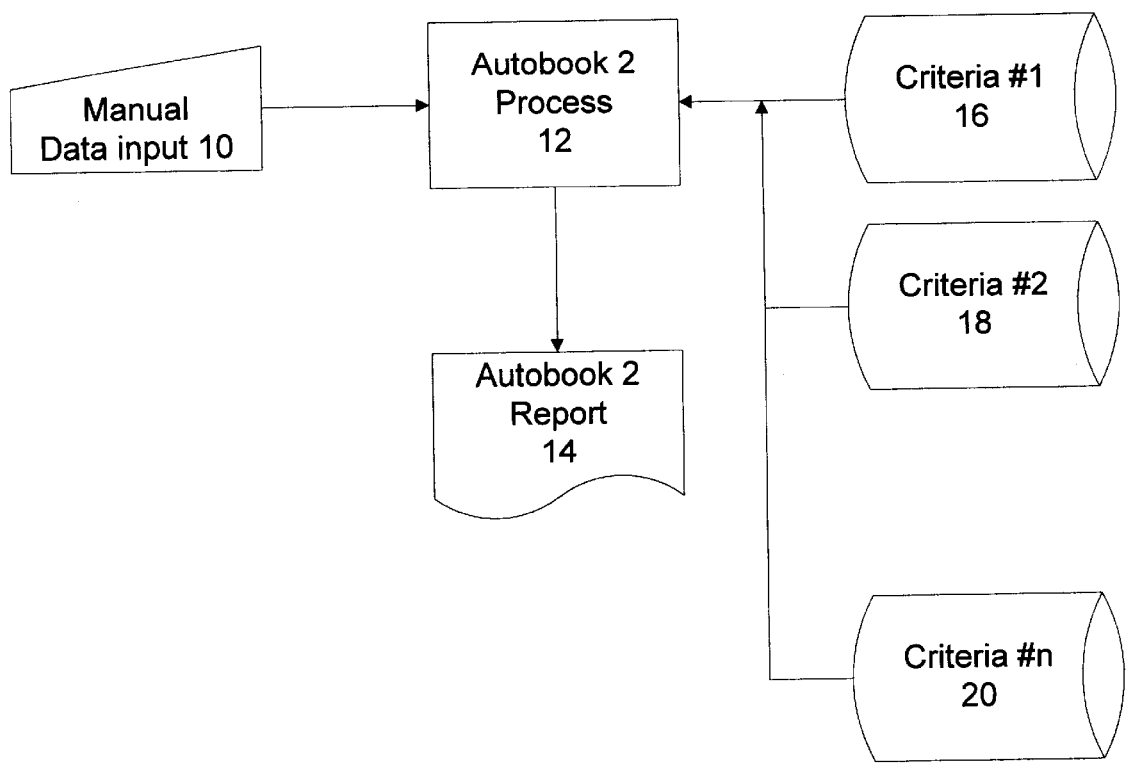
FIG. 2 depicts a block diagram showing the major components of the system.

FIG. 2 depicts a block diagram showing the major components of the invention. The system, known as AUTOBOOK 2®, is based on a set of knowledge bases called criteria sets 16, 18, and 20. These represent an indefinite number of criteria sets, since the system is not limited to the use of a particular set of these.

Each criteria set represents a particular domain within the health care context. For instance, the criteria set known as ISP is the knowledge base used in conjunction with the surgery domain. Similarly, ISX is used within the imaging domain, including technologies such as X-Rays, Magnetic Resonance Imaging, ultrasound, etc.

Still referring to FIG. 2, the AUTOBOOK 2 (12) process executes using the data within a selected criteria set in conjunction with a set of either manual data input 10, or linked data input 13 from a linked process In the case of linked data input, only the patient information and some of the procedure selection is automatically input. However the final selection of the procedure or body system data, as well as the criteria point selection, must always be manually input. The execution of the AUTOBOOK 2 process on such a criteria set produces a Review, which may be recorded in the form of an AUTOBOOK 2 Report 14, or may be exported in the form of a linked data output 15. The reviews are stored in the aggregation data base 11.

Figure 3:
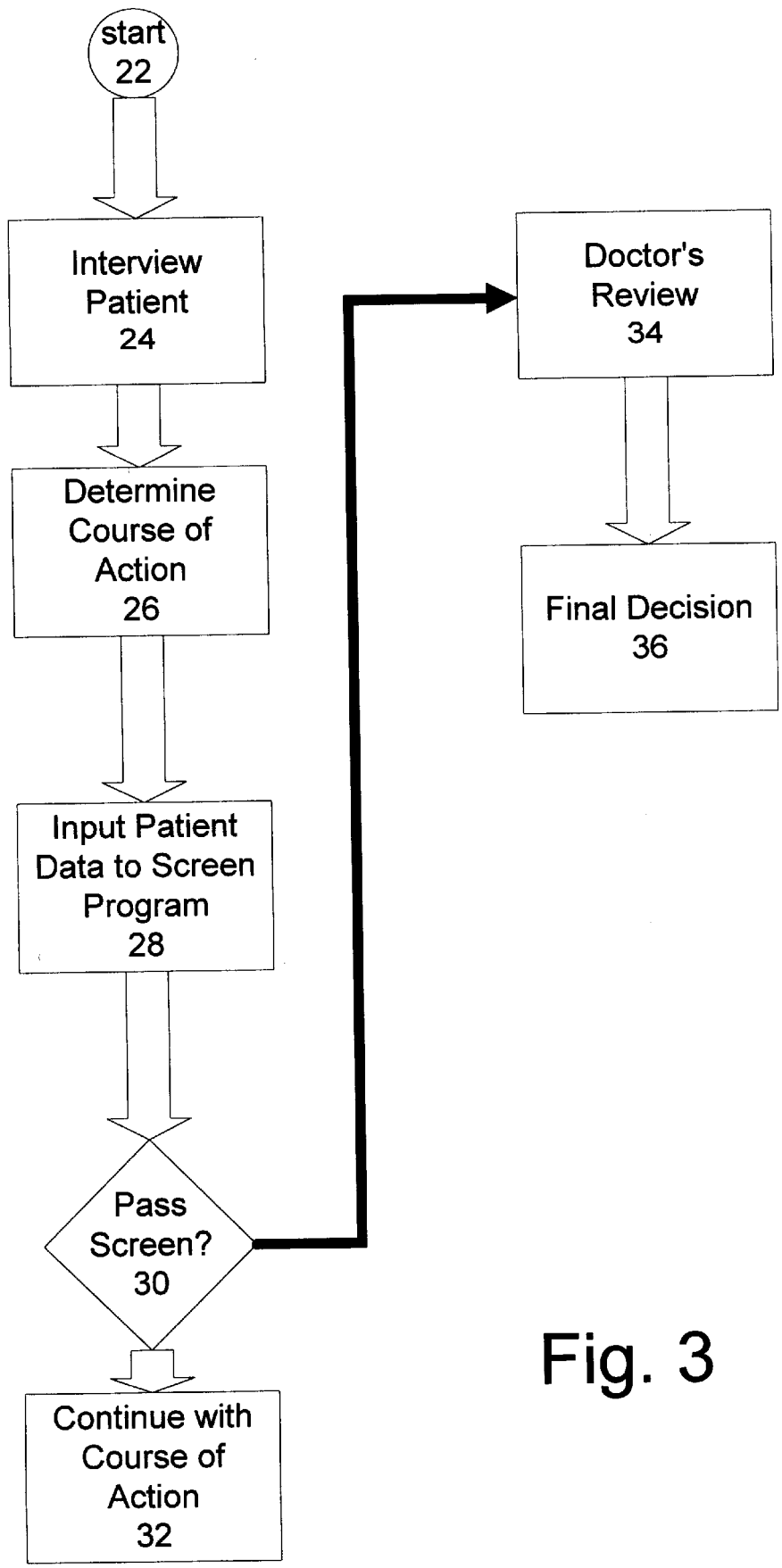
FIG. 3 depicts a high-level flow diagram of the system.

FIG. 3 shows how this system operates in real time. The user starts, by assessing the patient 22. This assessment is typically done by a physician. The physician determines a course of action 24 based upon the assessment. A nurse or physician's assistant next makes a phone call 26 to the payor (typically an insurance company or managed care organization) for authorization to proceed.

The next step is data entry 28, after which AUTOBOOK 2 will indicate either that the criteria have been met, or that they have not been met 30. If the criteria have been met, then the treatment may proceed as planned 32. But if not, the planned action must be reviewed 34, prior to the making of a final decision regarding the planned action.

Even when the criteria have been met, there are circumstances when a second level review is required. For instance, certain mandatory notes encountered during the review may call for a second level review. Furthermore, a reviewer or requester may, at his or her own discretion, request a second level review.

Basic Operation of AUTOBOOK 2

Figure 4:
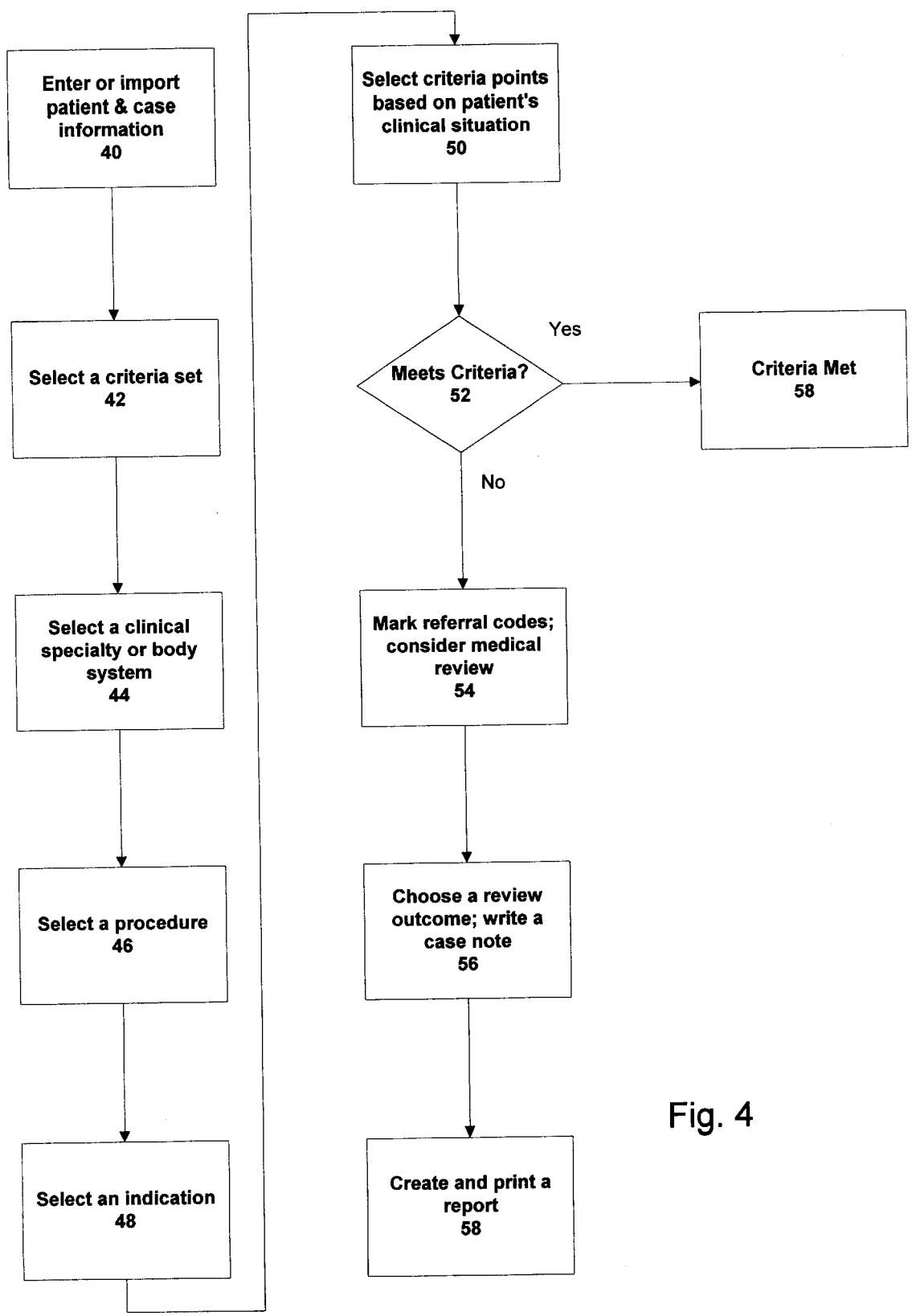
FIG. 4 depicts a low-level flow diagram of the system.

This process is described in greater detail by means of FIG. 4. Referring now to this figure, after the patient data is entered 40, the AUTOBOOK 2 user selects a criteria set 42. Available criteria sets include the following:

a) ISDa Intensity of Service, Severity of Illness, and Discharge Screens, adult
b) ISDp Intensity of Service, Severity of Illness, and Discharge Screens, pediatric
c) ISP Surgery and Procedures
d) ISX Indications for Imaging Studies and X-rays
e) IWC Indications for Workers' Compensation
f) IRM Injury Recovery Management
g) IPS Indications for Primary & Specialty Care Management
h) SIMplus Surgical Indications Monitoring Next, the user selects a clinical specialty or body system 44. These categories includes Cardiology, Neurosurgery, Opthalmology, and Urology. This clinical specialty is thus applied to the criteria set to further narrow the selection.

The user next selects a procedure 46 to further limit the selection. Examples of procedures are iridotomy, removal of cataracts, enucleation, blepharoplasty, etc. Following the procedure selection, the user selects an indication of the condition for which the intervention is proposed 48. Examples of conditions selected include:

a) cataract with reduced visual function;
b) cataract interferes with posterior pole procedure; and
c) cataract interferes with posterior pole observation.

Having input all the preceding information, the user then begins selecting criteria points based on the patient's clinical situation 50. Selection of these criteria points is done by the user via the various screens used for the data input, and which are described subsequently.

After the criteria points are thus selected, the system will make a determination 52 either that the criteria have been met 58 or that they have not been met. The reviewer will always choose a review outcome and may write appropriate case notes 56. If criteria have not been met, the user marks referral codes 54, and the case is referred for medical review.

Figure 5:
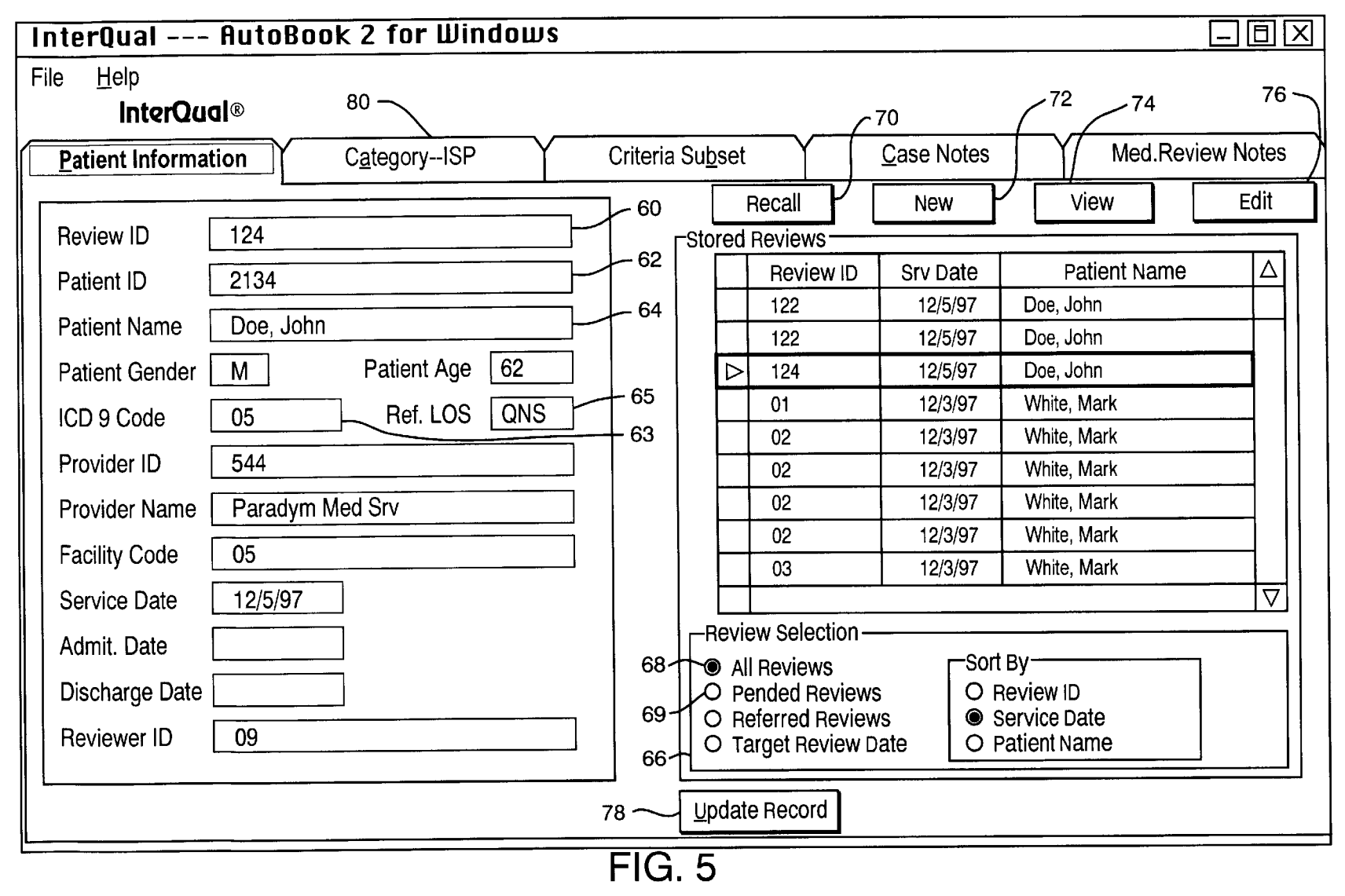

Finally, a report is created by the system, and it may be printed out 58, faxed, or e-mailed This process may be understood in more detail by referring now to the following figures. FIG. 5 shows the first substantive screen which appears on the computer monitor. This screen is used to input patient information, and is organized into several areas. These include the data input area, which contains data input boxes for the input of data such as Review ID 60, Patient ID 62, Patient Name 64, etc. To the right of the data input boxes is the Stored Reviews area 66, which contains a listing of previous reviews. The Review Selection area 68 is used as a filter to limit the reviews listed in the Stored Reviews area, and to change the order in which these reviews are presented within the Stored Review area. A number of buttons is provided, including the Recall 70, New 72, View 74, and Edit 76 buttons, with which the user may begin a new review, recall an existing review, view an existing review, or edit an existing review. The Update Record button 78 is used to update an existing data record contained within the data input area.

Figure 6:
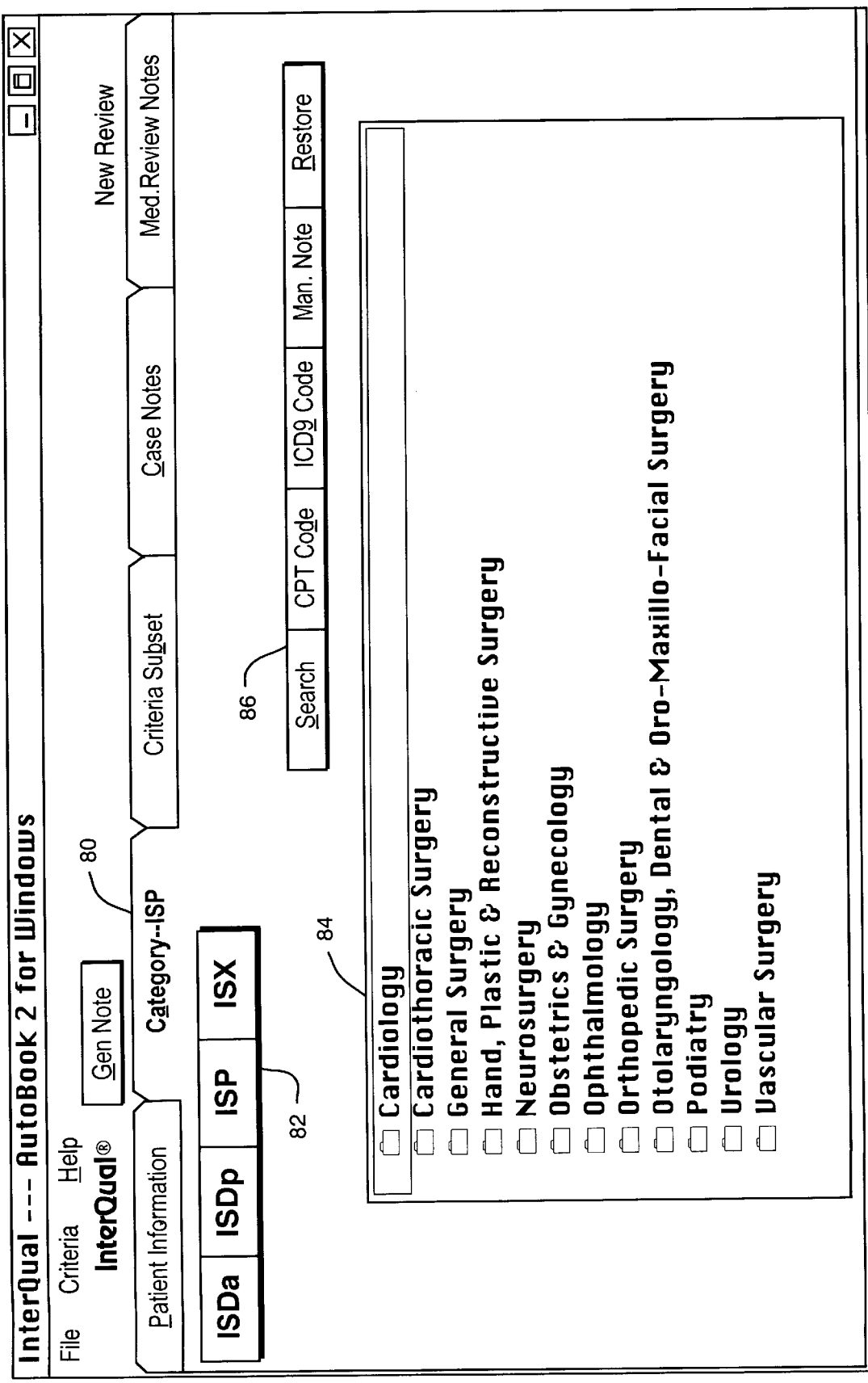
FIG. 6 depicts the Clinical Specialty/Body system screen for a sample ISP review.

In using this screen, the user may begin a new review by first clicking with the mouse on the New button, and then inputting the data into the data input area. When the data input is complete, the user clicks on the Category ISP tab 80, and the screen of FIG. 6 next appears. By use of this screen the user selects the criteria set 42, as seen in FIG. 4, using the buttons which appear at the top left of the screen. In this case, the user has clicked on the ISP button 82, indicating the Indications for Surgery and Procedures criteria set. The user may then make a selection from the Clinical specialty/Body System window 84 by double-clicking with the mouse on the selection. In the present example the user selects Cardiology, the first selection, and the next screen appears. The user may also find a selection not listed by using the Search button 86, which allows the user to enter the name of a procedure or body system.

Figure 7:
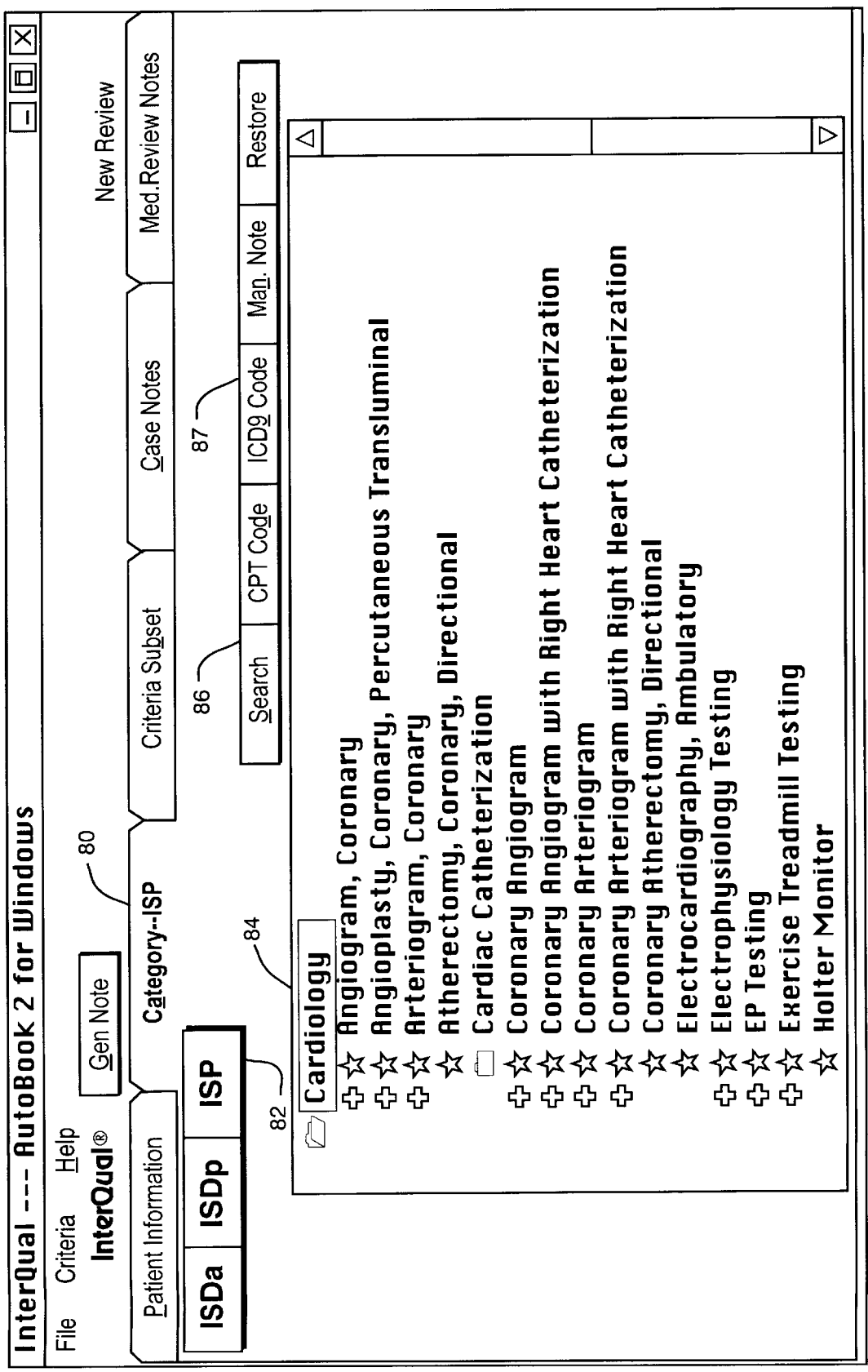
FIG. 7 depicts the Procedure screen for a sample ISP review.

FIG. 7 shows the next screen, which displays the selected Clinical specialty/Body System within the Clinical specialty/Body System window 84. The selection in this example is Cardiology, and the corresponding folder icon is now displayed as an "open" folder, with the contents of the selected folder appearing as indented headings. Each of these headings represents a particular procedure 46, as shown in FIG. 4, and for this example the user will select the first entry, "Angiogram, Coronary".

Figure 8:
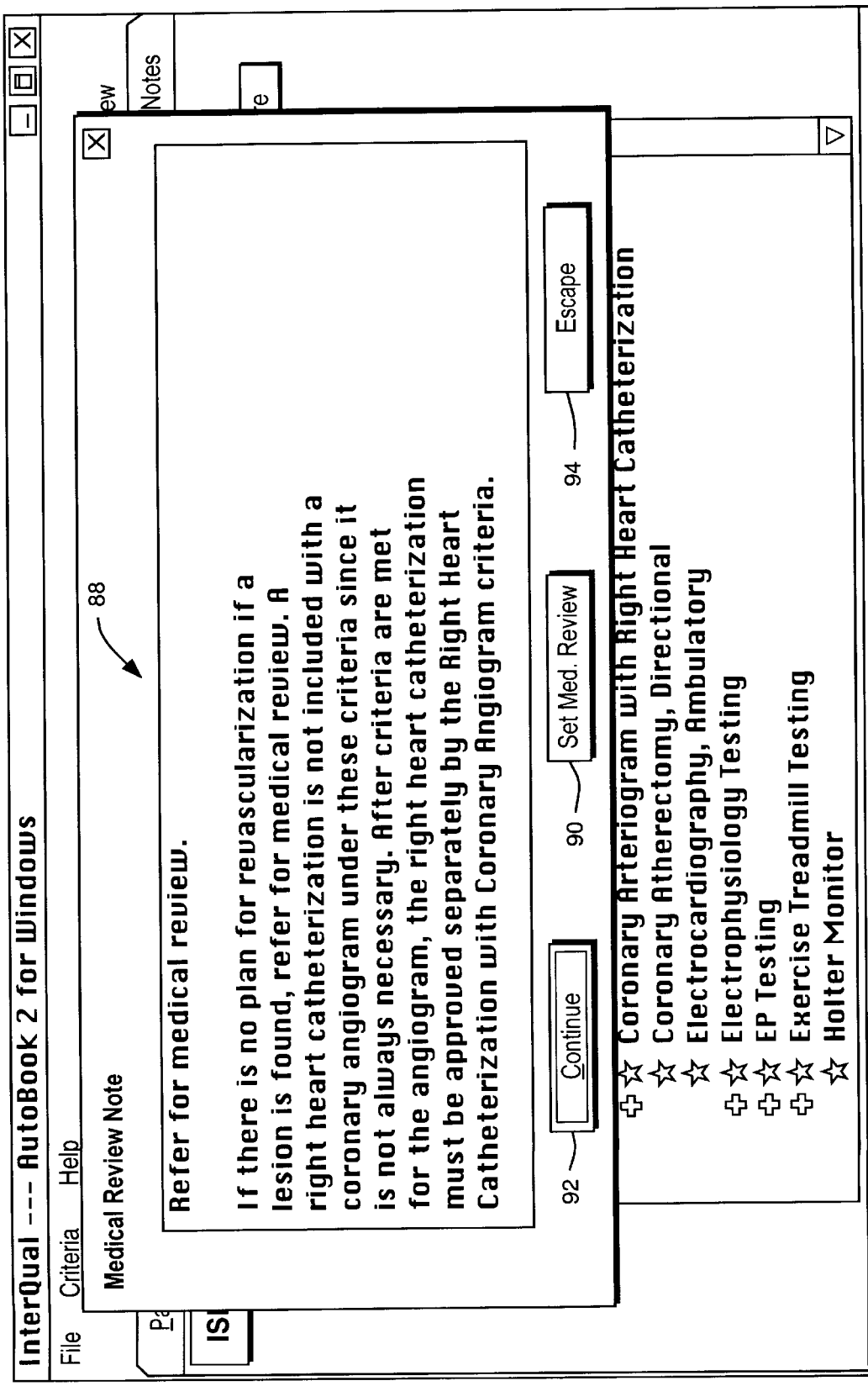
FIG. 8 depicts the Medical Review Note screen for a sample ISP review.

It should first be noted that this entry has a "+" symbol, as well as a "*" to the left of the words "Angiogram, Coronary". The "+" indicates there is a mandatory Medical Review Note associated with this entry. When the user selects this entry, by double clicking with the mouse, the note is displayed, as shown in FIG. 8. The note appears in a Medical Review Note window 88, which is displayed in the foreground on top of the preceding screen. The user may, in addition to other choices, click on the "Set Med. Review" button 90, which automatically flags this session for further review. The user may continue on to the next screen by clicking the "Continue" button 92, or may click the "Escape" button 94 and return to the previous screen.

The "*" indicates there is a discretionary note associated with this entry. Because it is discretionary, the user will not see this note unless he/she clicks on the "Gen Note" button 96, as seen in FIG. 9.

Referring now to FIG. 9, the next screen displayed allows the user to select an indication 48, as shown in FIG. 4, by means of the Indication window 98. Note that, in this window, symbols which appear to the left of the individual indication selections include a "*", an up arrow, a down arrow, and the bracket pair "[ ]".

In the example of FIG. 9, the top line appearing in the Indication window is labeled "100 Severe cardiac ischemia by stress test." The up arrow to the left of this line indicates that the line has been expanded, and the subsequent lines labeled 110 to 160 are the expanded sub-indications following. Each of these sub-indications in turn contain down arrows, showing that they, too, may be expanded.

By continuing to expand these indications as required, the criteria points are eventually reached. In FIG. 9 the line numbered 700 is a criteria point, as indicated by the bracket pair to its left. The bracket pair is selected by clicking with the mouse, which causes a check mark to be displayed within the bracket pair, as shown in FIG. 10.

Figure 10:
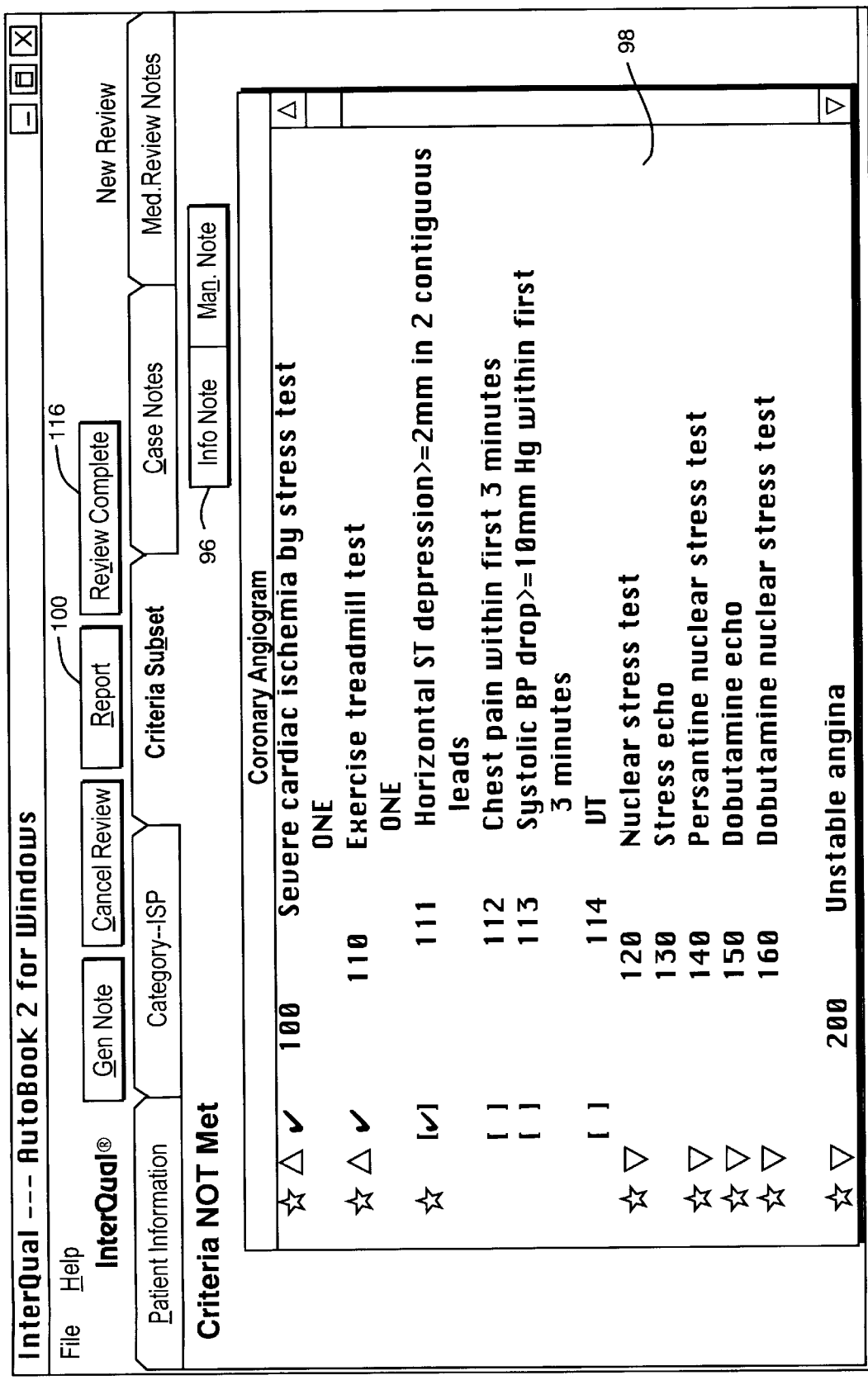
FIG. 10 depicts an expanded version of the Procedure/Indication screen for a sample ISP review.

In FIG. 10 the screen shows the indication lines expanded within the Indication window 98, and several indications checked. The indications are ranked by level, which are numbered: level 1, level 2, etc. Each succeeding level is indicated by a succeeding indentation on the Indication screen. Thus, within screen 98", the line labeled 100 is at level 1, the line labeled 110 is at level 2, and indented relative to level 1, the line labeled 111 is at level 3, and indented from level 2, and so forth.

Between the lines labeled 100 and 110 is the Rule, in this case labeled "ONE", indicating that one of the following lines on this level (sub-indications) must be selected to meet the criteria. Other Rules include TWO, THREE, ALL, etc., indicating which of the following indications must be selected to satisfy the criteria.

At this point the user selects a review outcome using the Case Notes tab 184, as seen in FIG. 22. The user in this figure has selected "Approved" from pull-down list 188.

Finally, the user may click the Report button 100 to request a report be generated summarizing the findings of the screening system. FIGS. 11 and 12 show the two pages of this report generated by the example herein. This report can also be printed on the computer printer 5 by clicking on the Print icon 110 of FIG. 11; it can be exported to a file by clicking on the Export icon 112; or it can be e-mailed by clicking on the E-mail icon 114. The user then terminates and saves the review for later examination by clicking on the Review Complete button 116 of FIG. 10.

ISD Criteria Set Embodiments

Among the criteria sets are those known as ISD. The ISD criteria sets are used to assist in assessing the appropriateness of a level of care based upon the patients clinical needs. The evaluations of ISD depend upon objective clinical information rather than upon a diagnosis. They are based upon the patient's episode of illness, current medication and treatment, and discharge readiness.

ISD includes the following components a) Intensity of Service—the care being provided the patient;

b) Severity of Illness—the symptoms and clinical findings indicating how sick the patient is; and c) Discharge Screening—the stability of the patient, the necessity of continuing care, the appropriateness of the patient leaving his/her present care level.

d) Prerequisites—the non-patient specific factors, such as availability of physicians, alternate power sources, etc., for treatment at this level of care.

There are presently different ISD criteria sets for adults and pediatric patients.

Figure 13:
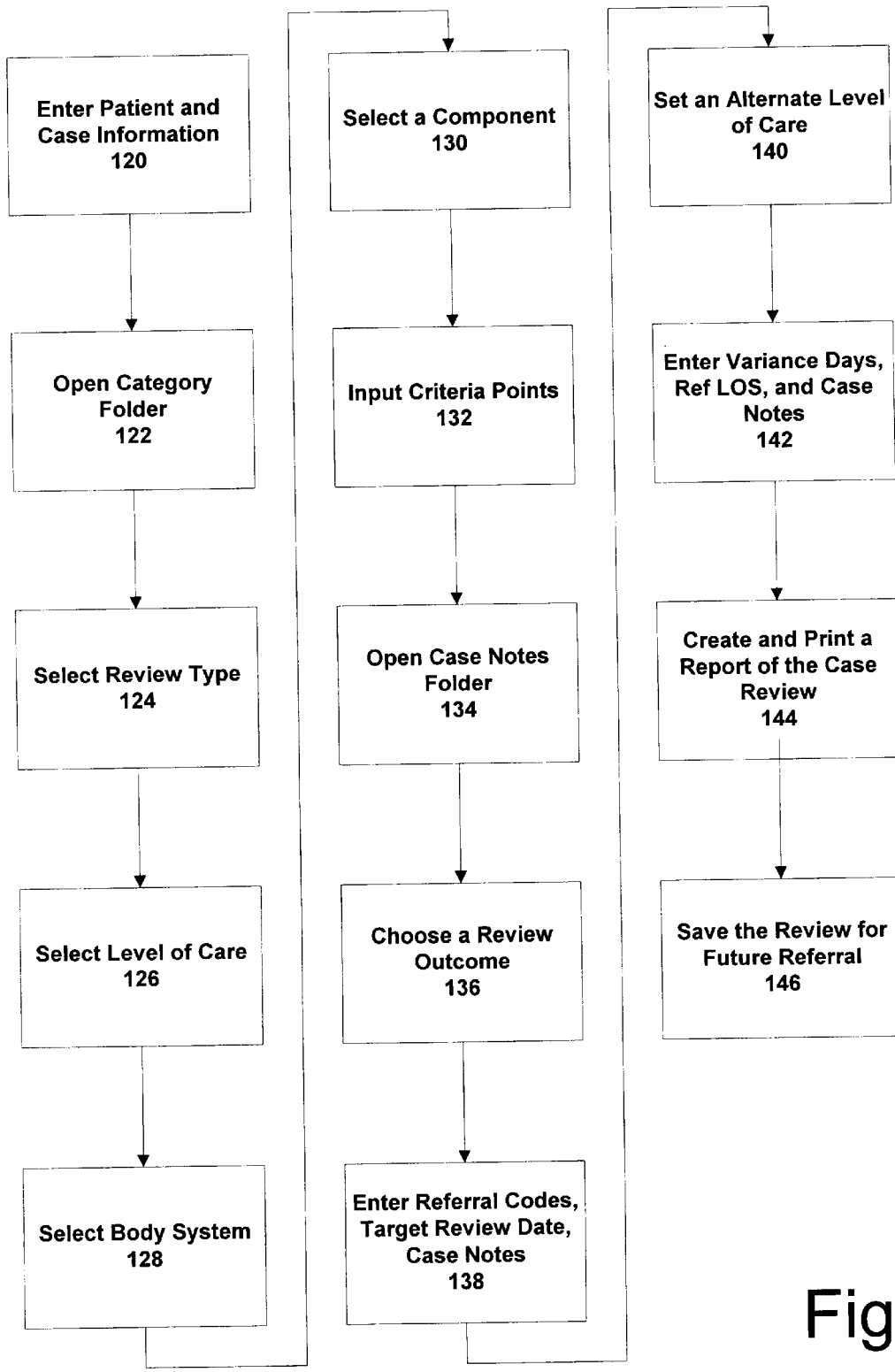
FIG. 13 depicts a flow diagram for a sample ISD review.

FIG. 13 shows the steps used in performing an ISD review using AUTOBOOK 2. The first step is the entering of the Patient and Case Information 120. Next the user opens the category folder 122, and selects a Review Type 124. Review types include:

a) PRE—preadmission;

b) ADM—admission;

c) SUB—subsequent; and d) DIS—discharge.

Next, a level of care is selected 126. Level of care includes: Critical, Acute, Rehabilitation, Subacute, and Home Care. Then a body system is selected. Body systems available include the blood/lymph/immune system, the cardiovascular system, the eye, ear, nose, and throat, etc. Then the user proceeds to the first Component 130. Components include Prerequisites, Severity of Illness, Intensity of Service, or Discharge. There may be an additional component following, depending upon the review type. If a second component is called for, the user will select this second component.

The criteria points are then input 132, at which point the system indicates either a Criteria Met or Criteria Not Met condition. If the Criteria Met condition appears, then the level of care planned and described is medically appropriate, and vice versa.

Next, the Case Notes Folder is opened 134, and a Review Outcome is chosen 136. Review Outcomes include Approved, Referred for Medical Review, Awaiting More Information, etc. Then Referral Codes, Target Review Date, and Case Notes are entered 138. Alternate level of Care 140, and Variance Days, Ref LOS, and Case Notes are also entered 142.

Finally, a report is created and printed 144. The review is then saved for possible future referral 146.

Figure 14:
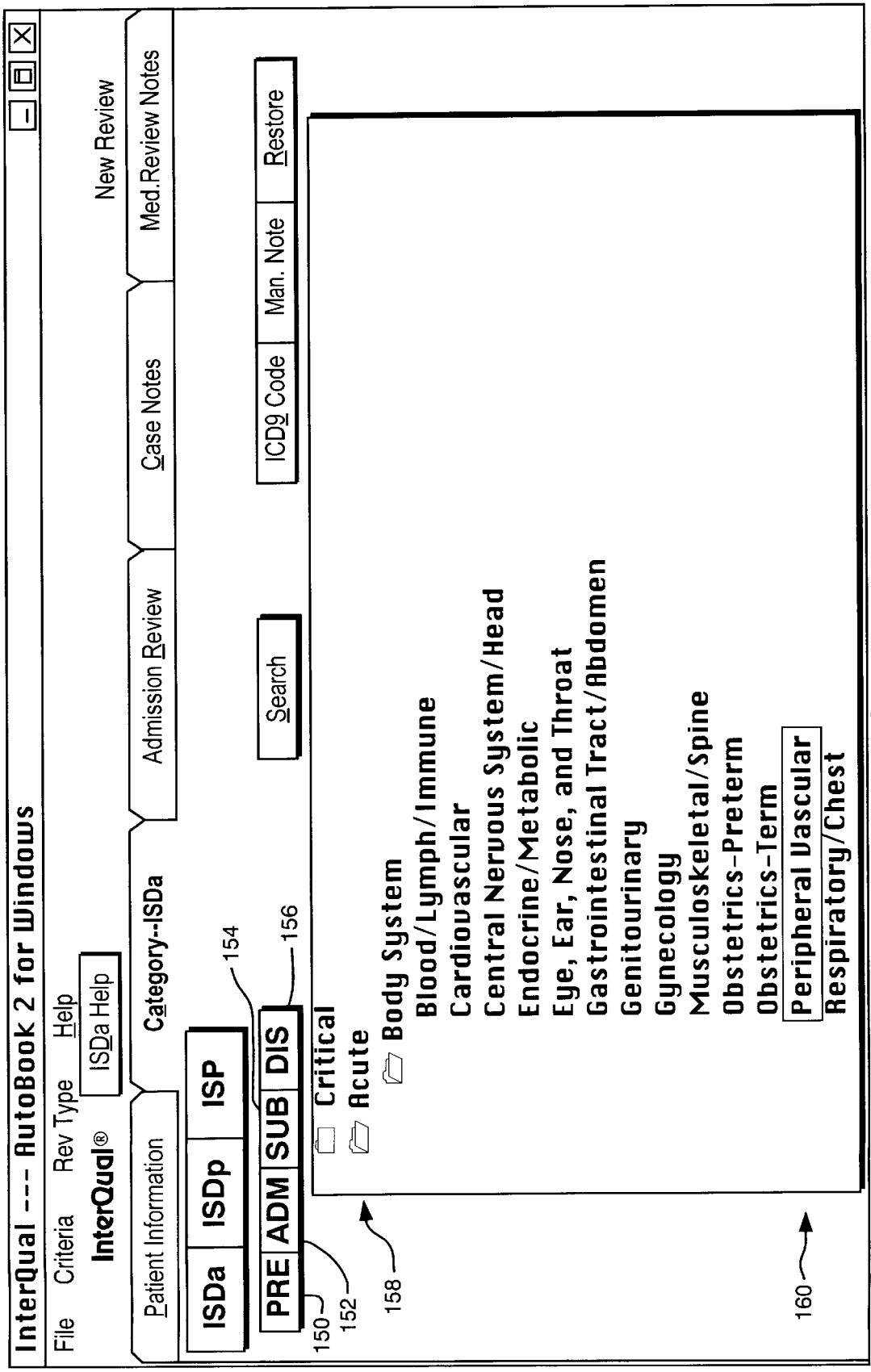
FIG. 14 depicts the Level of Care/Body System screen for a sample ISD review.

This process may be understood in more detail by referring now to the following figures. FIG. 14 shows the Category-ISD screen which appears on the computer monitor after the entry of the Patient Information. The four Review Type buttons appear as PRE 150 (preadmission), ADM 152 (admission), SUB 154 (subsequent), and DIS 156 (discharge). ADM has been selected in the example, as reflected by the depressed appearance of the ADM button.

Still referring to FIG. 14, the Acute level of care 158 has been selected, and the Peripheral Vascular 160 body system has been selected by double clicking with the mouse.

Figure 15:
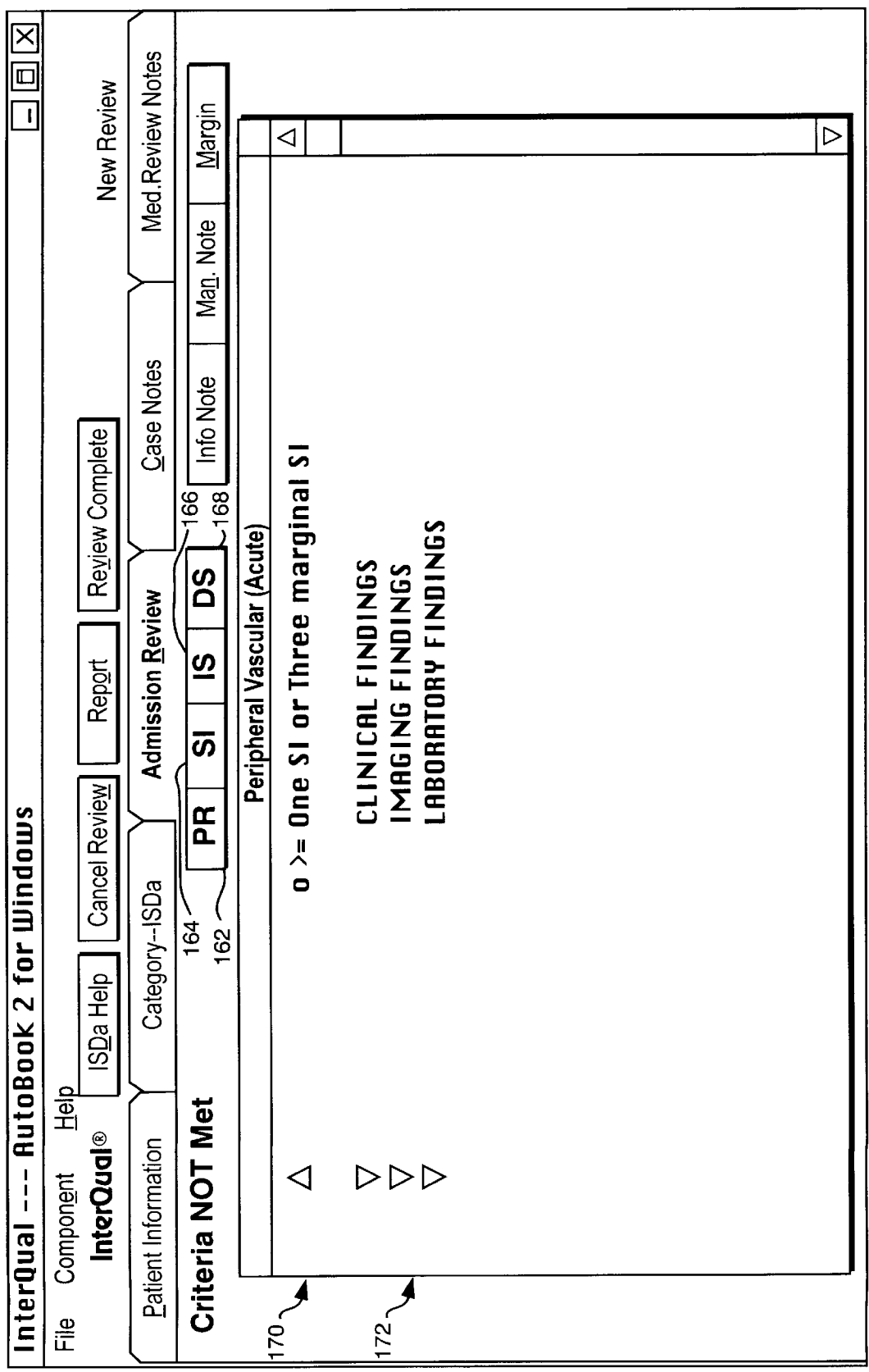
FIG. 15 depicts the Admission Review screen for a sample ISD review.

Upon selecting the body system, the Admission Review folder is opened, and the Admission Review Screen appears, as seen in FIG. 15. The component buttons PR (prerequisites) 162, SI (Severity of Illness) 164, IS (Intensity of Service) 166, and DS (Discharge Screening) 168 appear, and SI is selected, as seen by the depressed appearance of the SI button.

Figure 16:
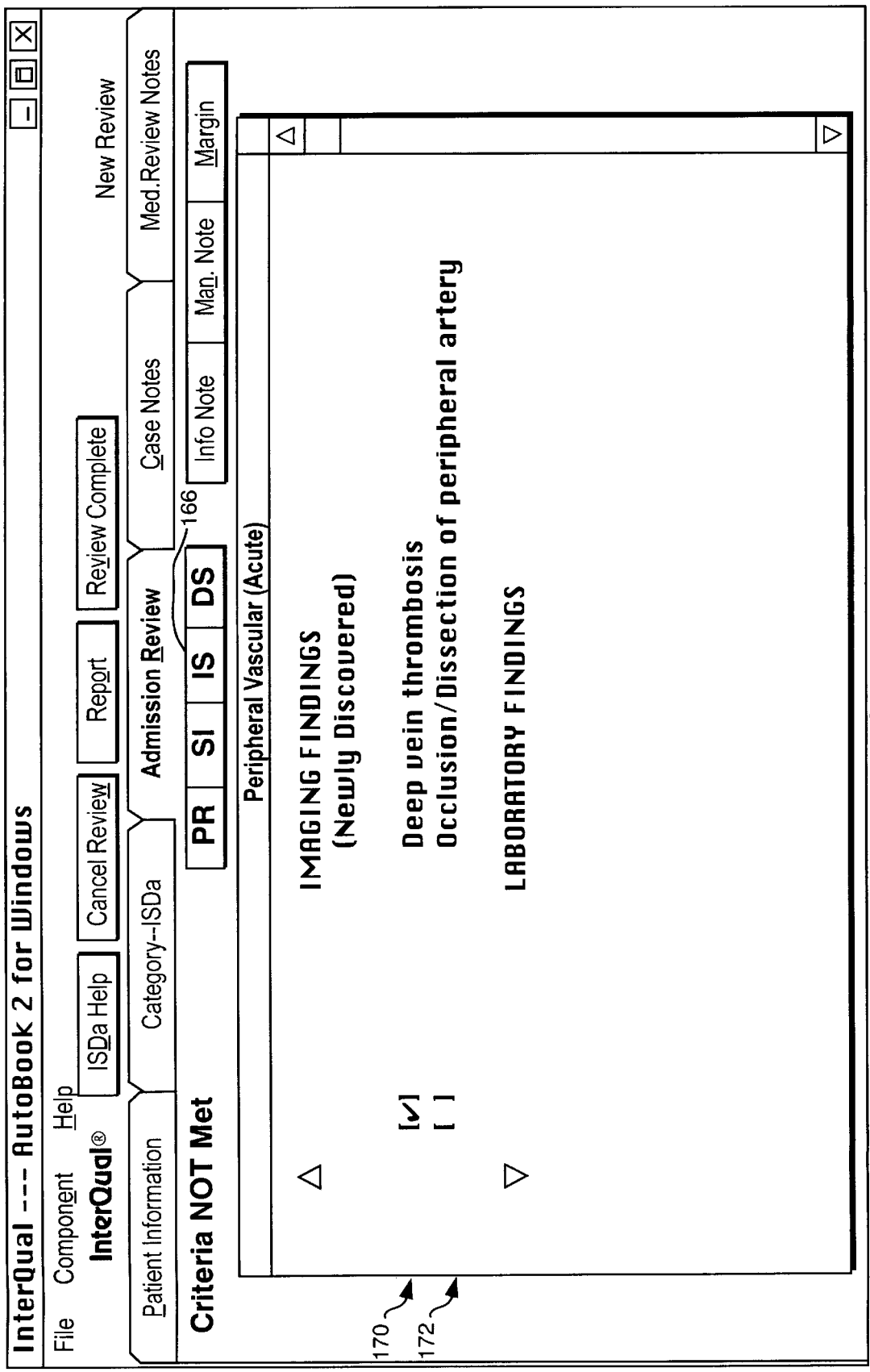
FIG. 16 depicts the Admission Review screen for a sample ISD review, showing criteria points.

Next, the criteria which are true for the patient are selected. The Rule is displayed 170, and the Clinical Topic "Imaging Findings" is selected by means of a mouse click. As a result, the "Imaging Findings" clinical topic is expanded, as shown in FIG. 16, allowing the user to input Criteria Points 170 and 172.

Figure 17:
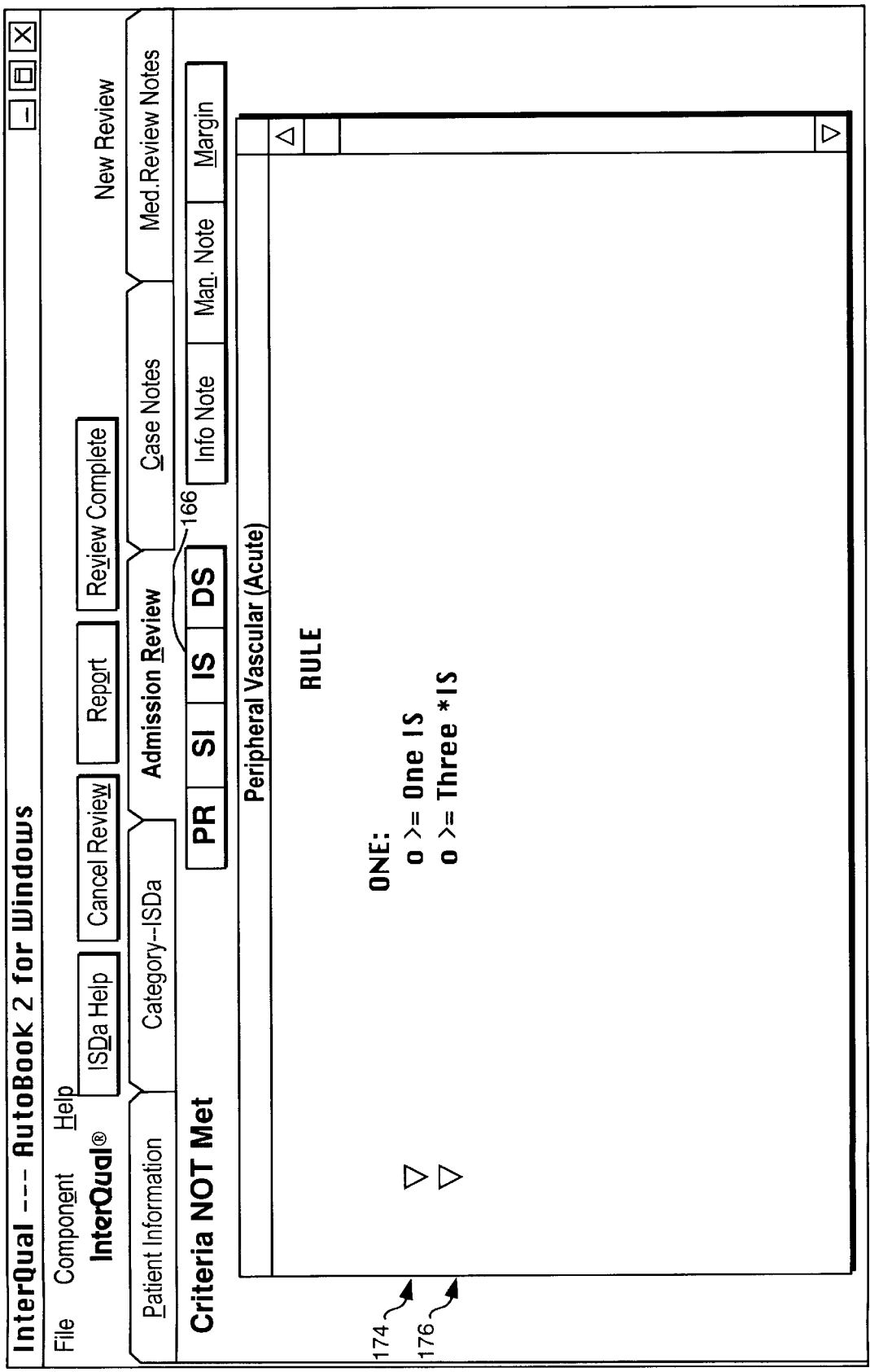
FIG. 17 depicts the Admission Review screen for a sample ISD review, with a RULE displayed.

The user next clicks the IS button, and the screen of FIG. 17 appears, showing the Rule that either one of the two conditions 174, 176 must be TRUE. By double clicking on the down arrow 174, the line is expanded to display the various Criteria Points available, as seen in FIG. 18.

By clicking on the DVT protocol <=3d line 176, the user sets this criteria point to TRUE, and the CRITERIA MET display 178 appears, indicating that admission to the proposed level of care in this case is medically appropriate.

Figure 18:
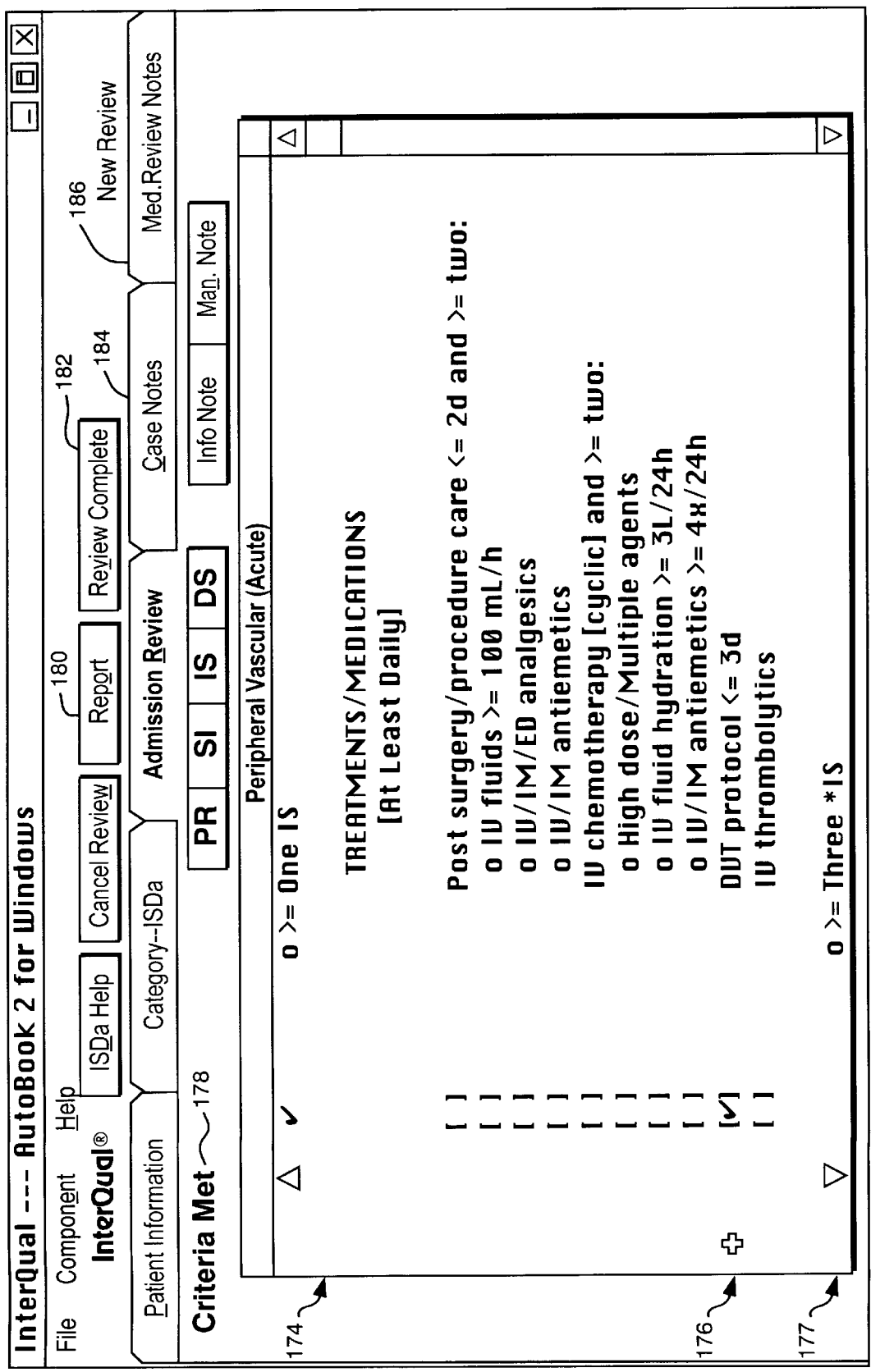
FIG. 18 depicts the Admission Review screen for a sample ISD review, with Criteria Met condition.

FIG. 18 demonstrates the use of "star IS criteria points". Referring to FIG. 18, the entry 177 is entitled "o>=Three *IS. The *IS represents services which may be safely administered at lower levels of care but which, in aggregate, three or more, will warrant the additional monitoring associated with the proposed level.

A report may be generated by clicking on the Report button 180, although this step is discretionary. The review is saved by clicking on the Review Complete button 182. The review will then be available for subsequent examination when desired.

IWC—Worker's Compensation Criteria Sets

An additional category provided is identified by the acronym IWC, or "Indications for Workers' Compensation". IWC is actually a collection of criteria sets, the collection including IRM (injury recovery management), and subsets of the ISD, ISP, and ISX criteria sets. These subsets function identically to the fully-functional versions of these criteria sets, as previously described.

Figure 20:
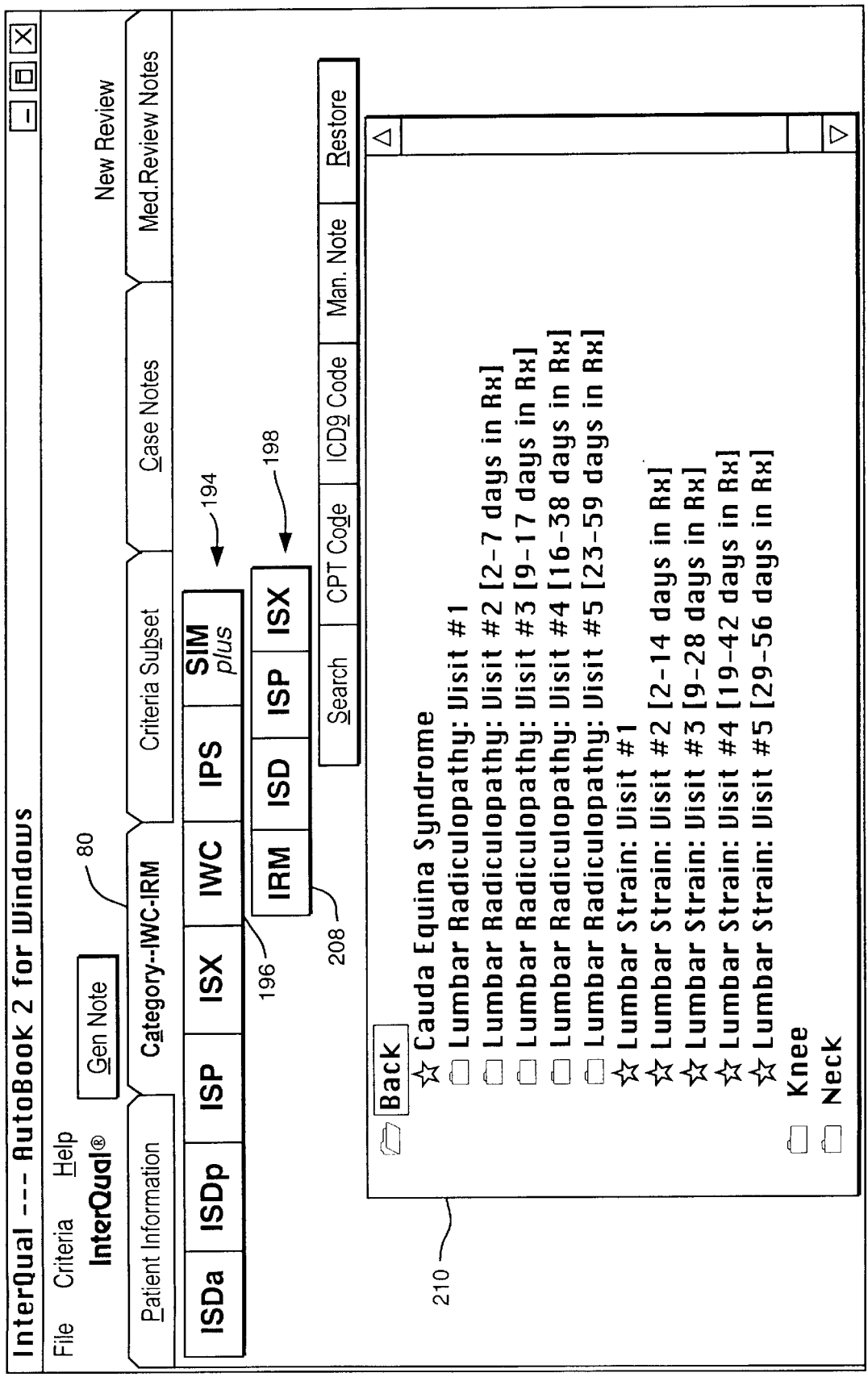
FIG. 20 depicts an Indications for Worker's Compensation screen, with cascaded menus displayed.

IWC is entered by clicking on the Category tab 80 which appears in FIG. 5. The result is the screen shown in FIG. 20. Referring now to FIG. 20, the category buttons 194 include the IWC button 196, which is shown depressed to indicate that it has been previously selected. Directly below the IWC button is a row 198 of four buttons labeled IRM, ISD, ISP, and ISX, which are used to select the corresponding criteria sets. In FIG. 20 IRM has been selected, as seen by the depressed appearance of the IRM button 200.

The cascading menu text screen 210 of FIG. 20 corresponds to the IRM function selected. The entries on this menu screen are organized into body systems, which, in turn are organized into classes of procedures. Upon selecting the "Back" entry (line 1 of screen 210), and further selecting the "Cauda Equina Syndrome" (line 2 of this screen), a new screen appears as shown in FIG. 21.

Pended Reviews

AUTOBOOK 2 has the ability to suspend reviews pending more information. Although under normal circumstances the user will want to complete a review at a single sitting, there are circumstances which require information not currently available to complete a review. Reviews may be pended (suspended) by using the Case Notes or Med. Review Notes screens.

Referring to FIG. 18, the Case Notes tab 184 is clicked, resulting in the display of the Case Notes screen, FIG. 19. In FIG. 19 the Review Outcome pulldown menu 188 has been expanded, and the "Awaiting More Information" entry shown 192. The user has also checked the "Diagnostic service delay" Referral Code 190, indicating the reason for the delay.

The Med. Review Notes screen has similar capabilities, and is accessed by clicking the Med. Review Notes tab 186, as shown in FIG. 18.

Pended reviews may be selected for review by means of the Patient Information screen, as shown in FIG. 5. The Review Selection area 68 contains a radio button entitled "Pended Reviews" 69. When this button is checked, the only reviews listed in the "Stored Reviews" area 66 are those reviews which are pended by the first reviewer.

Reviews which have been either pended by the medical reviewer, or referred by the first level reviewer and not processed by the second level reviewer, are filtered by the "Referred" radio button.

Report Generation

The reports generated by AUTOBOOK 2 are a key element in the review process. These reports not only allow the monitoring of the progress of a medical treatment. They also provide a means for creating a repository of knowledge.

For instance, the performance of different doctors within the same environment can be compared. As an example, if a particular doctor is ordering 300% more x-rays than the average, this result can be detected by amassing the reports and subjecting them to analysis. Similarly, the system can generate utilization reviews to assess and monitor under-utilization and over-utilization.

AUTOBOOK 2 allows the data which constitute the individual reports to be output in two different ways. First of all, the data can be exported to a disk file, by clicking on the Export icon 112, as shown in FIG. 11. The user may choose any one of a number of different formats for the export, including ASCII, tab-separated ASCII, and WORK FOR WINDOWS® formats.

The data making up a report can also be E-mailed by clicking on the e-mail icon 114 as shown in FIG. 11. Data exported by e-mail may be formatted in any of the same formats available when exporting to a disk file.

The ability of AUTOBOOK 2 to export data allows the utilization of third-party report writers.

Linkages to Other Systems

AUTOBOOK 2 is written in Visual Basic®. As a result, the program has the ability, through Microsoft's OLE2® facility, to link its input and output to other programs. This facility makes it possible, for instance, to automatically enter data from an external process, and to automatically feed back the results into the same external process. As a result, AUTOBOOK 2 may be easily embedded in other HIS systems.

WINDOWS, WINDOWS 95, WINDOWS 98, WINDOWS 3.1, and WORD FOR WINDOWS are registered trademarks of Microsoft Corporation.

Import of Data

AUTOBOOK 2 has the facility to import standard LOS (length of stay) codes corresponding to user-entered ICD9 diagnosis or procedure codes. These parameters are displayed in the Patient Information screen shown in FIG. 5 as data input boxes 63 and 65.

The ICD9 Code may be entered by clicking on the ICD9 Code button 87 shown in FIG. 7.

While the invention has been described with reference to specific embodiments, it will be apparent that improvements and modifications may be made within the purview of the invention without departing from the scope of the invention defined in the appended claims.

We claim:

1. A computer-based medical screening system for use in medical facilities which reviews an intended course of action regarding a patient, accumulates data during the course of action, and provides information as to the utilization of medical resources during said course of action, the system comprising:

a knowledge base of medical information organized into criteria sets, the knowledge base comprising clinical specialties, body systems, procedures, indications, and criteria points, and wherein each criteria set contains data and rules for determining when the intended course of action is medically appropriate;

means for inputting patient information;

means for selecting a clinical specialty or body system;

means for selecting a procedure within the selected clinical specialty or body system;

means for selecting an indication within the selected procedure;

means for selecting criteria points within the selected indication based on the patient's clinical situation;

means for determining, based on the selected criteria points, whether or not the intended course of action is medically appropriate;

means for displaying the rules governing said determination;

means for recording the steps of the review process;

means for playback of the steps of the review process;

means for including one or more rationale review notes in the criteria sets;

means for associating rationale review notes with procedures, indications, criteria points and rules;

means for outputting the rationale review notes; and means for outputting one or more resource utilization reports.

2. The system of claim 1, wherein the rationale review notes further comprise mandatory rationale review notes and discretionary rationale review notes, and further comprising, for each type of rationale review notes, means for associating the rationale review notes with procedures, indications, criteria points and rules;

means for indicating the presence of said rationale review notes in association with a selected procedures, indications, criteria points and rules; and means for requesting the display of the rationale review notes.

3. The system of claim 2, wherein the criteria sets further comprise:

Intensity of Service, Severity of Illness, and Discharge Screens for adults;

Intensity of Service, Severity of Illness, and Discharge screens for pediatric patients;

Indications for surgery and procedures;

Indications for imaging studies and X-rays;

Indications for Workers' Compensation;

Indications for primary and specialty care management; and

Surgical indications monitoring.

4. The system of claim 3, wherein the means for inputting patient information comprises linking to an external program, and wherein the means for reporting the steps of the review process further comprises data linking means to a second external program, and further comprising an aggregation data base which contains a history of the reviews performed.

5. The system of claim 4, further comprising means for suspending a review and completing the review at a later time.

6. The system of claim 5, wherein the criteria points comprise "star IS" criteria points, which have a lesser weight in the processing means than other criteria points.

7. A medical screening method for use in medical facilities which comprises:

creating a knowledge base of medical information organized into criteria sets, the knowledge base comprising clinical specialties, body systems, procedures, indications, and criteria points, and wherein each criteria set contains data and rules for determining when the intended course of action is medically appropriate;

inputting an intended course of action regarding a patient;

inputting and accumulating patient data before and during the course of action;

outputting indications as to whether the intended course of action is appropriate;

outputting rationale review notes;

outputting information as to the utilization of medical resources during said course of action.

8. The method of claim 7, further comprising:

organizing the database into clinical specialty or body system subsets;

organizing the specialty or body system subset into procedure sub-subsets;

organizing the procedure sub-subset into indication sub-subsets; and organizing the indication sub-subsets into criteria point sub-sub-subsets s sub-subsets.

9. The method of claim 8, wherein the method is implemented by means of computer software.

10. A computer-software-based medical screening method for use in medical facilities, which comprises the following steps, in sequence:

entering patient and case information;

opening a category folder;

selecting a review type from the category folder;

selecting a level of care from the review type folder;

selecting a body system from the level of care folder;

selecting a component from the body system folder;

selecting a component from the body system folder;

inputting criteria points from the body system folder;

opening the case notes folder;

calculating a review outcome from the patient and case information, category folder opened, review type folder opened, level of care folder opened, body system folder opened, component folder opened, and criteria point selected;

opening the case notes folder;

entering referral codes, target review dates, and case notes;

setting an alternative level of care;

entering Variance Days, Reference LOS, and Case notes;

creating an printing a case review report; and saving the review for future referral.

11. A computer-based medical screening system for use in medical facilities which reviews an intended course of action regarding a patient having a clinical situation, and comprising:

a knowledge base of medical information organized into criteria sets, the knowledge base comprising clinical specialties, body systems, procedures, indications, and criteria points, and wherein each criteria set contains data and rules for determining when the intended course of action is medically appropriate;

means for inputting patient and case information;

means for selecting a review type;

means for selecting a level of care within the review type;

means for selecting a body system within a level of care;

means for selecting a component within a body system;

means for selecting an indication within the selected component;

means for selecting criteria points within the selected indication based on the patient's clinical situation;

means for determining, based on the selected criteria points, whether or not the intended course of action is medically appropriate;

means for displaying the rules governing said determination;

means for recording the steps of the review process;

means for playback of the steps of the review process;

means for including one or more rationale review notes in the criteria sets;

means for associating the rationale review notes with procedures, indications, criteria points and rules;

means for outputting the rationale review notes; and means for outputting one or more resource utilization reports.

12. The system of claim 11, wherein the rationale review notes further comprise mandatory rationale review notes and discretionary rationale review notes, and further comprising, for each type of rationale review notes, means for associating the rationale review notes with procedures, indications, criteria points and rules;

means for indicating the presence of said rationale review notes in association with a selected procedures, indications, criteria points and rules; and means for requesting the display of the rationale review notes.

13. The system of claim 12, wherein the criteria sets further comprise Prerequisites, Severity of Illness, Intensity of Service, and Discharge.

14. The system of claim 13, wherein the means for inputting patient information comprises linking to an external program, and wherein the means for reporting the steps of the review process further comprises data linking means to a second external program, and further comprising an aggregation data base which contains a history of the reviews performed.

15. The system of claim 14, further comprising means for suspending a review and completing the review at a later time.

16. The system of claim 15, wherein the criteria points comprise "star IS" criteria points, which have a lesser weight in the processing means than other criteria points.

* * * * *